(12) United States Patent
Vega et al.

(10) Patent No.: US 9,433,449 B2
(45) Date of Patent: Sep. 6, 2016

(54) INTRAMEDULLARY NAIL SYSTEM INCLUDING TANG-DEPLOYMENT SCREW WITH MALE INTERFACE

(71) Applicant: Orthopedic Designs North American, Inc., Tampa, FL (US)

(72) Inventors: Luis Vega, Tampa, FL (US); Lance Fagan, Tampa, FL (US)

(73) Assignee: ORTHOPEDIC DESIGNS NORTH AMERICA, INC, Tampa, FL (US)

( * ) Notice: Subject to any disclaimer, the term of this patent is extended or adjusted under 35 U.S.C. 154(b) by 49 days.

(21) Appl. No.: 14/505,103

(22) Filed: Oct. 2, 2014

(65) Prior Publication Data

US 2015/0038968 A1 Feb. 5, 2015

Related U.S. Application Data

(63) Continuation-in-part of application No. 13/445,954, filed on Apr. 13, 2012, now Pat. No. 8,491,584, and a continuation-in-part of application No. 13/713,560, filed on Dec. 13, 2012, now Pat. No. 8,876,822.

(51) Int. Cl.
*A61B 17/72* (2006.01)
*A61B 17/74* (2006.01)

(52) U.S. Cl.
CPC ......... *A61B 17/7266* (2013.01); *A61B 17/744* (2013.01)

(58) Field of Classification Search
CPC ..................... A61B 17/7266; A61B 17/744
USPC ............ 606/62–68, 304, 313, 323, 326, 327
See application file for complete search history.

(56) References Cited

U.S. PATENT DOCUMENTS

| | | | |
|---|---|---|---|
| 2,998,007 A | 2/1956 | Herzog | |
| 3,986,504 A | 10/1976 | Avila | |
| 5,645,589 A | 7/1997 | Li | |
| 5,702,215 A | 12/1997 | Li | |
| 5,976,139 A | 11/1999 | Bramlet | |
| 6,077,264 A | 6/2000 | Chemello | |
| 6,183,474 B1 | 2/2001 | Bramlet et al. | |
| 6,443,954 B1 | 9/2002 | Bramlet et al. | |
| 6,447,546 B1 | 9/2002 | Bramlet et al. | |
| 6,488,684 B2 | 12/2002 | Bramlet et al. | |
| 6,554,833 B2 | 4/2003 | Levy et al. | |
| 6,575,973 B1 | 6/2003 | Shekalim | |
| 6,648,889 B2 | 11/2003 | Bramlet et al. | |

(Continued)

*Primary Examiner* — Pedro Philogene
*Assistant Examiner* — David C Comstock
(74) *Attorney, Agent, or Firm* — Larson & Larson, P.A.; Justin P. Miller; Patrick A. Reid

(57) ABSTRACT

The Intramedullary Nail System including Tang-deployment Screw with Male Interface includes a nail for insertion into the intramedullary canal of the femur and a lag screw for insertion through the nail, into the femoral head of the femur. The nail is held within the intramedullary canal of the femur, affixed internally by the lag screw and tangs, without the use of screws that penetrate the surface of the bone, and without requiring significant x-ray exposure.

For nails of small diameter, a coupler, with two female ends, allows the diameter of the male/female interface between the driver and the actuator, which in turn extends the tangs, to be increased. This increase is possible because the lower section of the nail, where the talons are stored prior to extension, is of a larger diameter than the remainder of the nail.

13 Claims, 17 Drawing Sheets

(56) References Cited

U.S. PATENT DOCUMENTS

| | | |
|---|---|---|
| 6,695,844 B2 | 2/2004 | Bramlet et al. |
| 8,439,916 B2 * | 5/2013 | Coati ................. A61B 17/7258 606/62 |
| 8,491,584 B1 | 7/2013 | Fagan |
| 2002/0032445 A1 | 3/2002 | Fujiwara |
| 2006/0229617 A1 | 10/2006 | Meller et al. |
| 2008/0161805 A1 | 7/2008 | Saravia et al. |
| 2013/0325072 A1 | 12/2013 | Tan |

* cited by examiner

INTRAMEDULLARY NAIL SYSTEM INCLUDING TANG-DEPLOYMENT SCREW WITH MALE INTERFACE

CROSS-REFERENCE TO RELATED APPLICATIONS

This application is a continuation-in-part of pending U.S. application Ser. No. 13/713,560, filed on Dec. 13, 2012, which in turn is a continuation-in-part of U.S. application Ser. No. 13/445,954, filed on Apr. 13, 2012, and issued as U.S. Pat. No. 8,491,584, the disclosures of which are hereby incorporated by reference.

FIELD

The present invention relates to an intramedullary system for coupling a first and second portion of bone across a fracture.

BACKGROUND

Intramedullary nails were first used in the 1930s. These early nails were inserted into the intramedullary canal of the femur. The result was immediate fixation of femur fractures, resulting in reduced patient recovery time, increased mobility, and increased quality of life. Multiple examples of such nails are present in the prior art.

But rotation of the inserted nails was a problem because rotation would result in the nail being in a position different than that chosen by the surgeon. To address this issue, wires and/or screws were used to fix the rotational position of the nail with respect to the bone. The screws were installed through the outer surface of the bone, and required additional holes through the bone to allow the wire or screws to reach the nail.

These additional screws often had associated plates, changing the profile of the bone, potentially causing irritation to surrounding tissue.

The most significant problem caused by the requirement of additional fasteners is the additional time required under exposure to x-ray radiation. X-ray radiation is damaging to the patient, but is especially troublesome to the surgeon because each surgeon must perform many of these surgeries.

What is needed is a system that will provide support and positioning to a bone during patient recovery, while being minimally invasive, and with minimal side effects for the patient and surgeon.

SUMMARY

Description of the surgical technique is useful to understand many of the unique features present in the disclosed device. The technique described below will be directed at implantation into a human femur, but a similar technique is employed for other uses.

First, the patient needs to be positioned. The patient will take a supine position. Traction is applied to the affected leg, and the unaffected leg adducted and slightly rotated. This position creates a clear view for radiography of the affected leg and hip area. The head of the femur can now be exposed.

If the nail is to be installed in a humerus, the nail is implanted through a penetration in the proximal end of the humerus, passing through one or more fracture lines.

The description below addresses implantation into a femur, but humeral implantation is similar.

Next, the starting position for implantation needs to be determined. When viewing the femur from its proximal end, the entry point is nearly in-line with the medullary canal, or marrow cavity of the bone. There is a slight deviation due to the bend in the nail body.

Next, a curved entry awl, or trocar tip guide and power driver, is used to create a hole in the proximal end of the femur Next, the nail length must be determined. To provide support the nail must pass the fracture line. Additionally, the distal end of the nail, where the nail tangs are located, must be placed in an area of bone of sufficient diameter to allow for extension of the nail tangs without worry of penetrating the complete thickness of the bone. A metal guide, which is visible on an x-ray image, is held over the bone to compare the bone width to the required width shown by the metal guide. In combination with a long guide wire and a guide wire ruler, the ideal nail length is determined.

Next, the nail of appropriate length is affixed to the guide assembly. The guide assembly is a handle used for nail installation and orientation, as well as lag screw alignment.

Next, the lag screw guide pin is installed. The nail is in final position within the bone, and the hole for installation of the lag screw needs to be created. Using the guide assembly, a lag guide sleeve is inserted, followed by the lag guide pin. The lag guide pin is pressed through the lateral cortex of the femur, taking care to avoid exiting through the femoral head.

Next, the drilling depth and lag screw size must be determined, in a similar fashion as was performed for the nail. When drilling depth and lag screw size have been determined, the hole is drilled for the lag screw.

Next, the lag alignment plug and deployment driver are passed over the guide wire, mating to the nail. The lag alignment plug prevents the nail from twisting during the next step.

Next, a nail deployment driver is inserted into the nail, mating with the coupler, the coupler in turn mating with the actuator screw of the opposing nail tangs.

There are two general ways in which the nail deployment driver can interface with the actuator screw. The first is when the nail deployment driver having a male connection, and the actuator screw having a female connection. The second is the opposite, with the nail deployment driver having a female connection, and the actuator screw having a male connection. While these options are reasonable for connections of a certain diameter, when space constraints result in small diameters, these two options may result in mechanical failure.

Small nail diameters are encountered in humeral implantation, as well as specialized nails. E.g., femoral nails for children.

Regardless of which of the two options is chosen, the limited inner diameter of the nail results in an interface between the male/female connections of a small diameter. With this small diameter, low torque values produce high shear values. The result is that the male/female interface may fail catastrophically. While only a nuisance in some applications, in the case of an intramedullary nail this may result in the surgeon being unable to complete extension of the nail tangs, and unable to retract the nail tangs. The result is that the nail is ineffective, but unremovable.

The use of a coupler provides an alternative to the options described above. A separate coupler, with two female ends, allows the diameter of the male/female interface to be increased. This increase is possible because the lower section of the nail, where the talons are stored prior to extension, is of a larger diameter than the remainder of the nail.

Installing a permanent coupler during manufacturing takes advantage of this increased diameter, the result being that higher torque values can be applied without causing failure of the interface.

Now interfaced to the coupler, the nail deployment driver is rotated, in turn rotating the coupler, which in turn rotates the nail actuation shaft. The interaction of the nail actuation shaft and nail tang threaded hubs causes the nail tang threaded hubs to move axially with respect to the actuator screw. This in turn causes the tips of the nail tangs, both distal opposing nail tangs and proximal opposing nail tangs, to extend beyond the nail portals. The nail tangs will begin to extend through the spongy cancellous bone. The surgeon must monitor the force, taking care to stop the extension of the tangs when the resistance increases sharply, indicating contact with dense cortical bone. Alternatively, the appropriate extension is determined using a torque limiter in conjunction with the nail deployment driver. Ceasing extension of the tangs prior to full deployment is permissible because full deployment is not necessary to affix the nail to the bone.

Next, a lag screw deployment driver is attached to the appropriate lag screw using the lag screw intermediate internal threads for attachment. The lag screw deployment driver incorporates a protruding feature that mates with the slots of lag screw body. This provides angular alignment between the lag screw deployment driver and the lag screw, and allows the lag screw deployment driver to rotate the lag screw during installation. The lag screw is pushed until the threads contact bone, and turned to thread into the bone. A depth gauge is used to prevent over-tightening and ensure parallel alignment of the plane of lag screw anti-rotation flats with the nail body proximal bore longitudinal axis. When the depth gauge shows full insertion, no further tightening is required. After the lag screw is implanted in its proper position within the femur, the proximal end of the lag screw remains partially or fully protruding from the nail body bore.

Next, the lag driver is inserted into the top of the nail. The driver is mated to the lock screw body, and then turned to seat the lock screw button against the anti-rotation flats of the lag screw. The lag driver is left temporarily in place.

Next, the lag talon deployment driver is passed through the lag screw body, threading into the lag screw tang body. The threaded tip of the lag talon deployment driver engages the internal threads of the lag screw tang body. As the lag talon deployment driver is turned, the lag screw tang body is drawn toward the nail body, forcing the tangs out through the lag screw tang portals. A secure installation does not require full deployment of the tangs.

Next, compression is optionally applied. To close a gap in a fracture, or apply compression to the fracture, the lag screw is drawn into the body of the nail. To create this compression, the lock screw button must first be disengaged to allow longitudinal motion of the lag screw, while still preventing rotation. Then, using a threaded knob, a pulling force is applied to the lag talon deployment driver that is braced against the nail. This force acts to pull the lag screw into the nail body until the appropriate amount of compression has been applied.

Next, the lag screw fixation type must be set. Regardless of whether compression is used, the lag screw must be set in either a fixed or sliding fixation type. A fixed lag screw position prevents both rotation and sliding of the lag screw relative to the nail body. A fixed position is achieved by fully tightening the lock screw button against the anti-rotation flat. A sliding lag screw position allows free lateral sliding of the lag screw, while preventing rotation. This is achieved by the lag screw incorporating tapered anti-rotation flats, with the larger breadth at the proximal end, the narrower breadth at the middle (toward the distal end).

Finally, the tools used for installation can be removed, and the optional proximal nail end cap installed to prevent tissue growth over the proximal end of the nail. While the nail is suited for permanent installation, if needed, the procedure is fully reversible. The nail tangs and lag screw tangs can be retracted, and all parts removed.

BRIEF DESCRIPTION OF THE DRAWINGS

The invention can be best understood by those having ordinary skill in the art by reference to the following detailed description when considered in conjunction with the accompanying drawings in which:

FIG. 20 illustrates a side view of the lock screw body of the .

DETAILED DESCRIPTION

Figure 1:
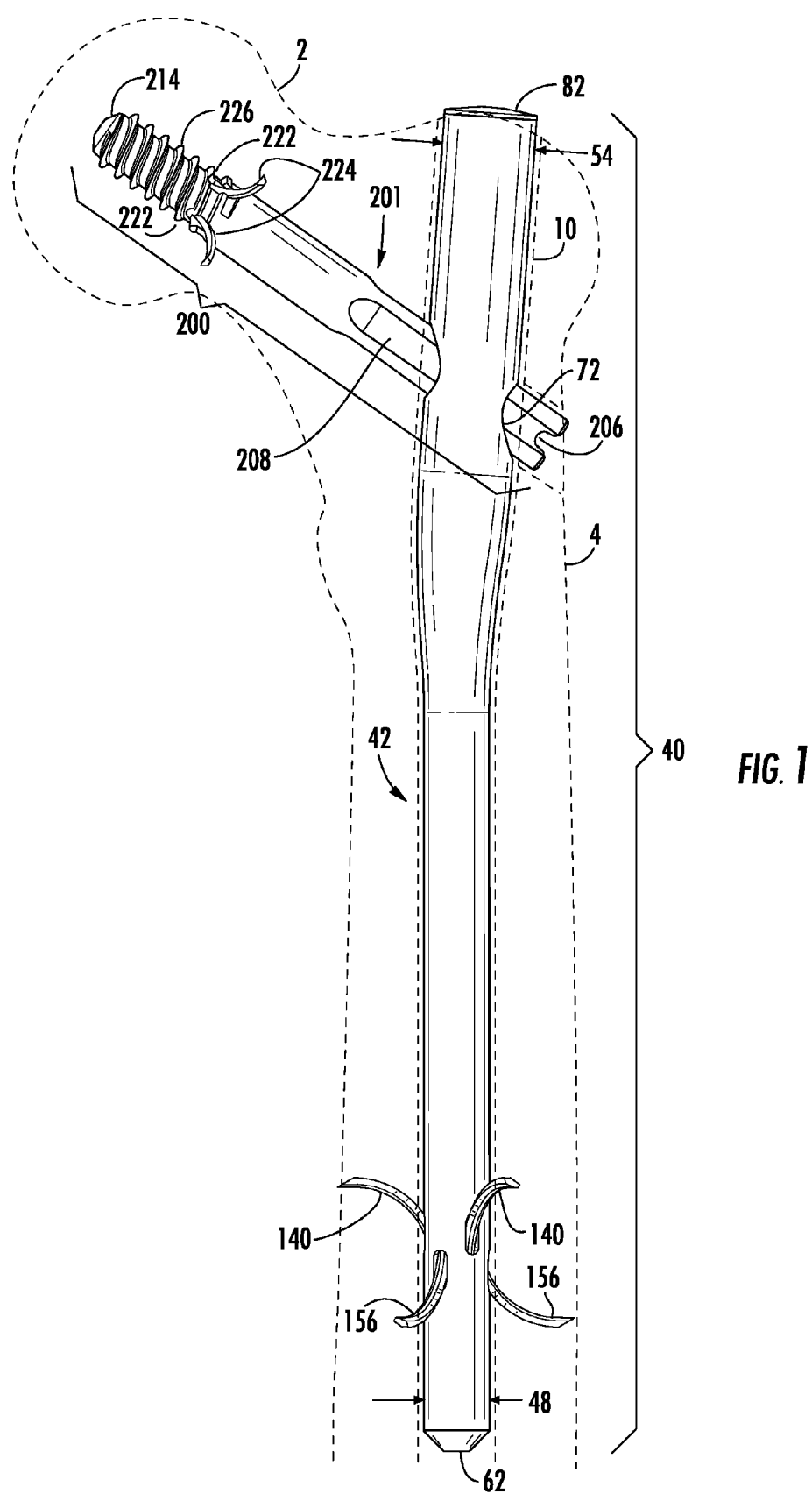
FIG. 1 illustrates an assembled view of a Intramedullary Nail System including Tang-deployment Screw with Male Interface.

Reference will now be made in detail to the presently preferred embodiments of the invention, examples of which are illustrated in the accompanying drawings. Throughout the following detailed description, the same reference numerals refer to the same elements in all figures.

The individual components of the assembly, as illustrated, are constructed of implantable grade titanium, but it is anticipated that any suitable material be used, such as implantable grade stainless-steel alloys or polymeric materials such as nylon, carbon fibers, and thermoplastics.

The Intramedullary Nail System including Tang-deployment Screw with Male Interface disclosed is especially suited for use fixing/stabilizing stable and unstable fractures of the upper portion of the femur. Exemplary, but not exclusive, examples of such fractures include intertrochanteric fractures, pertrochanteric fractures, high subtrochanteric fractures, low subtrochanteric fractures, and combinations thereof.

Much of the disclosure within the specification will relate to the use of the Intramedullary Nail System including Tang-deployment Screw with Male Interface to treat a fracture of a human femur. But the application of the Intramedullary Nail System including Tang-deployment Screw with Male Interface is not limited to such use, and is useful in other portions of the body and other species. The problems associated with conventional screws, and hardware external to the surface of the bone, are common to all bones within the body. It is anticipated that that the Intramedullary Nail System including Tang-deployment Screw with Male Interface be used with other bones of the body. The humerus, or upper arm bone, serves as an excellent example of an alternative use. The humerus has multiple nerves very close to the surface of the bone where traditional screws must be inserted, the screws often cause problems. The use of the Intramedullary Nail System including Tang-deployment Screw with Male Interface avoids such complications.

Referring to FIGS. 1-10, the first embodiment of the Intramedullary Nail System including Tang-deployment Screw with Male Interface will be described. The external features of the lag screw 200 include the lag screw body 201, lag screw end cap 214, lag screw threads 226, lag screw tangs 224, and anti-rotation flats 208. The external features of the nail 40 include the nail body 42, nail proximal end cap 82, nail lag screw transverse bore 72, distal opposing nail tangs 140, proximal opposing nail tangs 156, and nail distal end cap 62.

Further describing the lag screw 200, the lag screw body 200 has a plurality of lag screw tang portals 222, through which the lag screw tangs 224 can enter/exit the lag screw. The lag screw tangs 224 are fully retracted into the of the lag screw body 201 when the lag screw 200 is ready for use. The lag screw tangs 224 remain fully retracted until the lag screw 200 is fully positioned within the femoral head of the femur.

To deploy the lag screw tangs 224, a threaded driver (not shown) is inserted into the distal end of the lag screw 206. The threaded driver rests against a shoulder on the distal portion of the lag screw intermediate internal threads 218. Resting against the shoulder allows the threaded driver to provide axial force without itself moving. The threaded drive then engages the threaded hub of the lag screw tangs 224, causing the threaded hub to move longitudinally, in turn causing deployment of the tangs to begin.

During deployment, the lag screw tangs 224 extend through lag screw tang portals 222 and penetrate the cortical bone. This penetration greatly increases the mechanical connection between the bone and the lag screw. This mechanical connection also fixes the screw axially with respect to the bone to prevent unwanted rotation.

The lag screw tangs 224 are retractable, making removal of the lag screw 200 possible if it is ever required. This is done through a process similar to deployment. A second threaded driver (not shown) is inserted into the distal end of lag screw 200. Rather than resting on the shoulder of the distal portion of the lag screw intermediate internal threads 218, the second threaded driver engages the lag screw intermediate internal threads 218. And rather than engaging the threads of the lag screw tangs 224, the end of the second threaded driver presses against the hub, or another shoulder, of the lag screw tangs 224. Thus, as the second threaded lag screw driver threads into and through the lag screw intermediate internal threads 218, it presses against the hub of the lag screw tangs 224, causing the lag screw tangs to be pulled back into the lag screw 200.

Describing the lag screw threads 226, when the lag screw 200 is in use, the lag screw threads 226 engage the cancellous bone, or spongy bone. Cancellous bone makes up the inner portion of the femoral head of the femur, into which the nail is being installed in this example. The lag screw threads 226 are any type of threads, with either clockwise or counterclockwise thread rotation. The common direction, or handedness, for screw threads is right-handedness. A right-handed screw tightens when the head is turned clockwise, as viewed from overhead. Because it is more intuitive for a surgeon to use a right-handed thread, the lag screw threads 226 are right-handed in this embodiment. But left-handed threads are anticipated.

The lag screw threads 226 are of any form. This embodiment uses triangular threads.

Time in surgery is critical. The less time a patient remains under anesthesia, the safer the surgery. For this reason, among others, it is useful to decrease the time required to perform certain steps. One manner of decreasing the time required to install the lag screw 200 is to alter the lag screw threads 226. As is known, different screws often have different numbers of lead threads, where a single lead thread is a continuous thread that can be traced around the body of the screw. In some embodiments of the lag screw 200, there are two or more lead threads. Assuming that the axial distance between the threads remains consistent, this increases the speed at which the lag screw 200 can be installed because, all other factors being equal, a screw with two lead threads will penetrate at twice the speed of a screw with only a single lead thread.

After inserting the lag screw 200 and threading into the bone, the lag screw is optionally further secured. To do so, the lag screw tangs 224 are optionally extended. The lag screw tangs 224 pass through the lag screw tang portals 222. The surgeon must monitor the resistance during extension, taking care to stop the extension of the lag screw tangs 224 at the point the resistance increases sharply, indicating contact with cortical bone.

The lag screw 200 optionally includes lag screw end cap 214, which threads into lag screw distal internal threads 212, to prevent the intrusion of bone or soft tissue growth into the lag screw 200. Preventing such growth increase the chances of being able to remove the lag screw 200.

Now the nail 40 itself will be described. The nail is designed for insertion into the intramedullary canal of the femur, being anatomically shaped to match the axis of the canal, including a bend angle 44 between the nail body proximal centerline 52 and the nail body distal centerline 46. The nail body proximal outside diameter 54 is greater than the nail body distal outside diameter 48 to match the narrowing of the intramedually canal 42 within the femur 4. The larger nail body proximal outside diameter 54 is sized to accommodate the diameter of nail lag screw transverse bore 72 as well as diameter of nail proximal bore 80.

The lag screw centerline to nail centerline angle 230 is the angle between the nail body distal centerline 46 and the lag screw centerline 232. This angle 230 is chosen to match the angle of the femoral head with respect to the distal portion of the femur. When used for a human femur, this angle is approximately 125 degrees. The goal is to align the lag screw 200 with roughly the center of the femoral head. This position reduces the likelihood that the lag screw tangs 224 will break through the surface of the bone. But despite this preference, the ultimate position is within the surgeon's discretion based on the needs of the specific patient.

The nail proximal bore 80, nail distal bore 56, and nail distal end bore 60 are of any cross sectional shape. A circular cross section is shown in the figures, but in alternative embodiments other cross sections, such as square, oval, or star are used. Alternative cross sections are useful to allow inserted hardware to move through the nail body axially, but with a fixed rotational position.

The nail proximal internal threads 84 allow the optional nail proximal end cap 82 to be installed. While not required, installation of the nail proximal end cap 82 is recommended to prevent bony ingrowth, which would make removal of the Intramedullary Nail System including Tang-deployment Screw with Male Interface more difficult.

Figure 15:
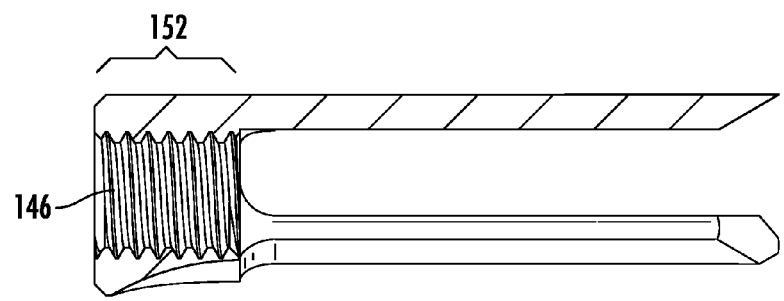
FIG. 15 illustrates a cross-sectional view of a nail tang.

Referring to FIGS. 3, 9-11, and 15-18 the operation of the nail tangs 140/156 will be described. The nail body 42 is locked within the bone by a pair of opposing nail tangs: the distal opposing nail tangs 140 and proximal nail tangs 156. The distal nail tangs 140 and proximal nail tangs 156 share a nail actuation screw 144. The distal opposing nail tangs 140 have a nail tang distal threaded hub 152, and the proximal opposing nail tangs have a nail tang proximal threaded hub 153. The nail tang distal threaded hub 152 interfaces with the nail actuator screw distal thread 160, and the nail tang proximal threaded hub 153 interfaces with the nail actuator screw proximal thread 158. FIG. 15 is a cross-section of a nail tang 140/156 with hub 152/153, showing the internal threads.

The nail actuator screw 144 has a nail actuator screw bore 146 to allow the nail actuator screw 144 to pass over a guide wire during installation.

The interaction of the nail actuator threads 158/160 and nail tang threaded hubs 152/153 causes the nail tangs 140/156 to simultaneously move along the length of the nail actuator screw 144 when the nail actuator screw 144 is turned. The nail actuator screw 144 is turned by inserting a tool into the nail actuator screw drive head 147. This in turn causes nail tang pre-curved tips 150 of each opposing distal nail tangs 140 and proximal opposing nail tangs 156, to extend beyond the nail portals 78. The nail actuator threads 158/160 have opposite threading (e.g., one is right-hand threaded, the other left-hand threaded), causing the nail tang threaded hubs 152/153 to move toward each other, or away from each other, when the nail actuator screw 144 is turned.

Figure 16:
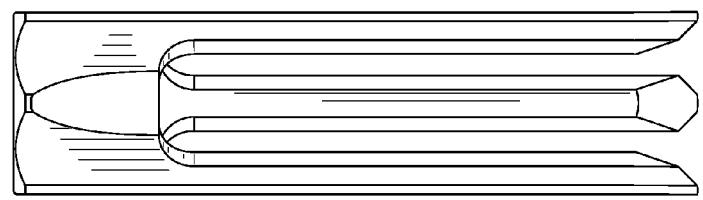
FIG. 16 illustrates a first side view of a nail tang of the Intramedullary Nail System including Tang-deployment Screw with Male Interface.
Figure 17:
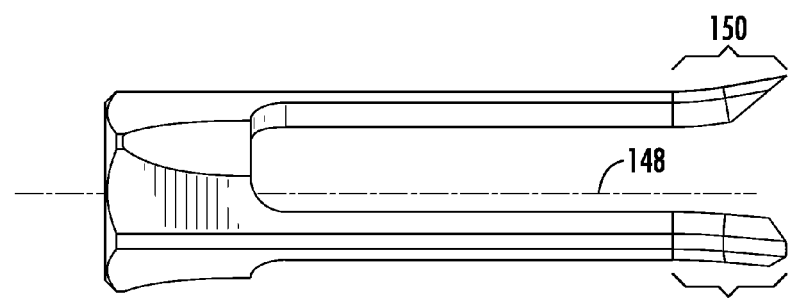
FIG. 17 illustrates a second side view of a nail tang.
Figure 18:
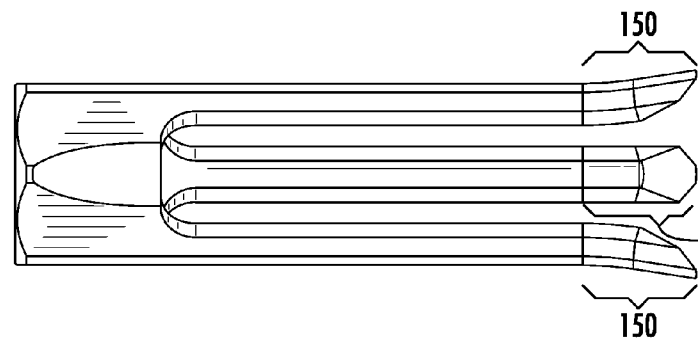
FIG. 18 illustrates a third side view of a nail tang. .
Figure 21:
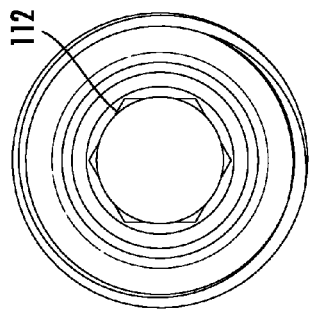
FIG. 21 illustrates an end-on view of the proximal end of the lock screw body.
Figure 20:
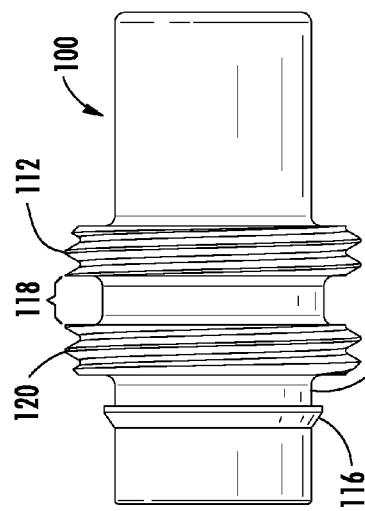
Figure 22:
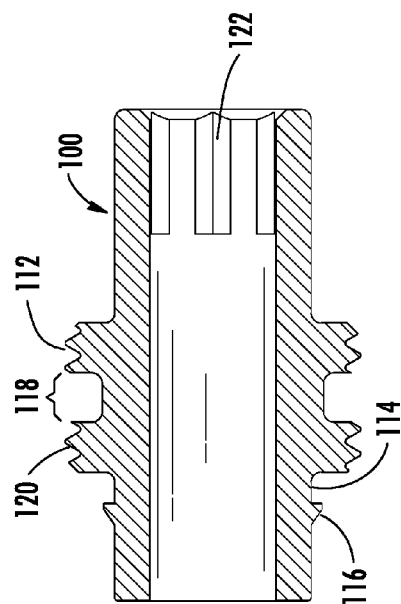
FIG. 22 illustrates a cross-sectional view of the lock screw body.
Figure 19:
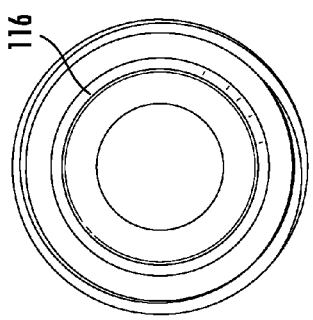
FIG. 19 illustrates an end-on view of the distal end of the lock screw body.
Figure 25:
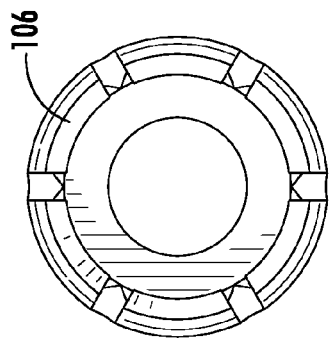
FIG. 25 illustrates an end-on view of the proximal end of the lock screw button.

The opposing nail tangs 140/156 are pre-curved before installation, meaning that as part of the manufacturing process, the nail tang pre-curved tips 150 of the opposing nail tangs 140/156 are bent away from the longitudinal axis of the nail tang body. FIG. 16 shows straight nail tangs 140/156 before bending into pre-curved tangs. FIGS. 17 and 18 show the tangs 140/156 after the tips have been bent to create the nail tang pre-curved tips 150.

The shape of the nail tang pre-curved tips 150 performs a number of functions: First, during assembly, when the opposing nail tangs 140/156 are moved into place in the distal portion of the nail body, the nail tang pre-curved tips 150 of the opposing nail tangs 140/156 snap, or pop, into their respective nail portals 78. The self-locating feature of the opposing nail tangs 140/156 with the nail tang pre-curved tips 150 simplifies assembly, and ensures that the tangs are properly located.

Second, in this installed position, the nail tang pre-curved tips 150 rest against the nail portal slanted surfaces 76. The nail portal slanted surfaces 76 serve to smoothly guide the opposing nail tangs 140/156 through their path to exit the nail 40. The pre-curved nature of the tips 150 begins the process of plastic deformation of the opposing nail tangs 140/156 as they exit the nail tang portals 78, guided by the nail portal slanted surfaces 76. The angle of the slanted surfaces 76 controls the shape of the opposing nail tangs 140/156 during the process of plastic deformation. Much as a die is used to create an extruded shape during extrusion, the shape of the nail portal 78 and angle of the nail portal slanted surface 76 serves to shape each opposing nail tang 140/156 as it passes through.

Third, the shape of the nail tang pre-curved tips 150 shape allows the opposing nail tangs 140/156 to be present in the nail tang portals prior to extension. This allows the opposing nail tangs 140/156 to almost immediately contact the interior surface of the bone. The result is a reduction in surgery time and fewer turns required prior to contact. As a result, the nail 40 is less likely to rotate out of place during actuation.

During the extension process, the nail tang threaded hubs 152/153 are guided within the nail distal shaped bore 66 by the nail tang retention grooves 86. The nail tang retention grooves 86 allow the nail tang threaded hubs 152/153 to slide axially along the nail body distal centerline 46, but prevent twisting with respect to the nail body distal centerline 46. As a result, the opposing nail tangs 140/156 exit the nail tang portals 76 within the same plane as the nail body distal centerline 46.

As they are extended, the opposing nail tangs 140/156 will begin to lock into the cancellous bone. During the operation, the surgeon will likely monitor the force, taking care to stop the extension of the opposing nail tangs 140/156 at the point the resistance increases sharply, indicating contact with cortical bone.

The proximal opposing nail tangs 156 exit the nail portals 78 toward the distal end 41 of the nail 40, producing a force that pushes the nail 40 toward the proximal end of the femur 4. The distal opposing nail tangs 140 exit the nail portals 78 toward the proximal end 88 of the nail body 40, producing an opposing force that pushes the nail 40 toward the distal end of the femur 4. Assuming a uniform interior bone surface, the net force is approximately zero, thereby maintaining the axial position of the nail as chosen by the surgeon.

Despite the net forces being nearly zero, there is likely a small axial force by the nail actuation screw 144 against its ends. This force is transmitted to the nail body 40 by, on the proximal end, the thrust washer 154, and on the distal end, the nail distal end cap 62. The thrust washer 154 is designed for operation under sliding friction and spreads out the compressive axial load, as is the nail distal end cap 62. The thrust washer 154 and nail distal end cap 62 also serve to keep the nail actuation screw 144 properly positioned relative to the distal end 41 and proximal end 88 of the nail 40.

Figure 12:
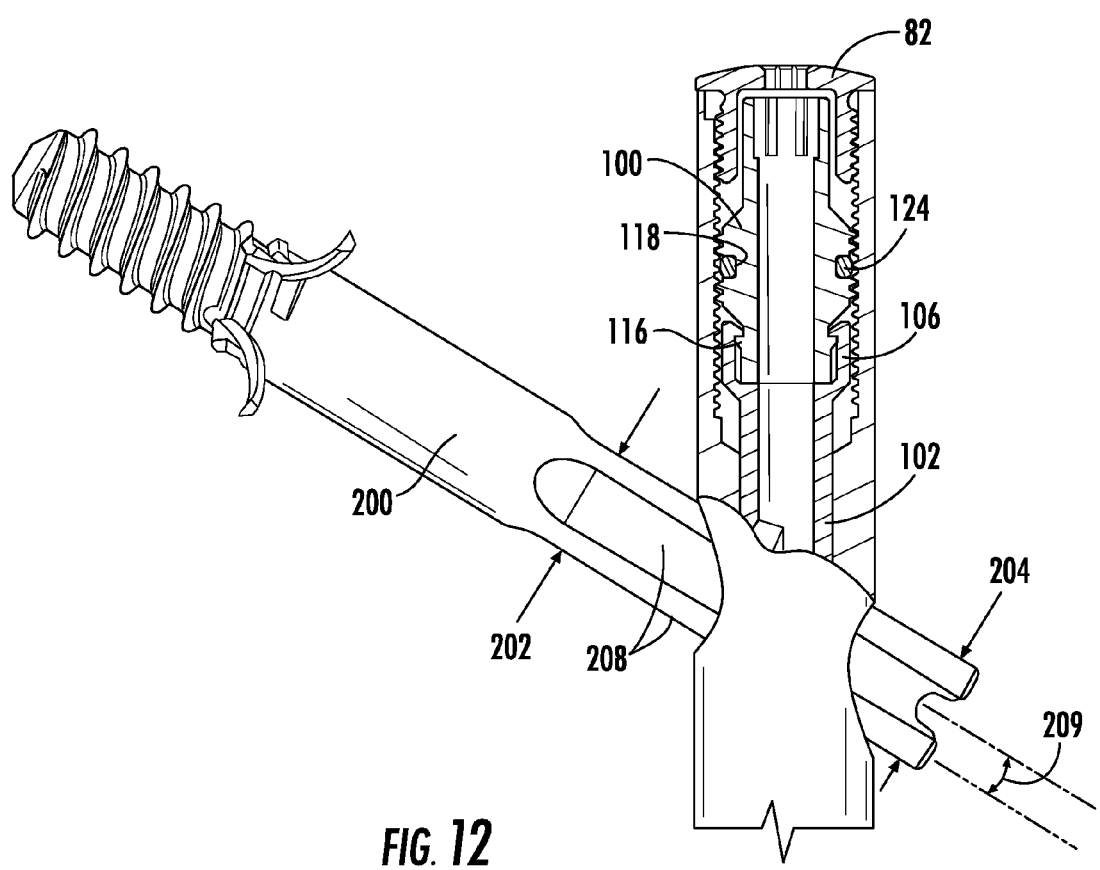
FIG. 12 illustrates a partial cross-section of the nail tang locking region of the Intramedullary Nail System including Tang-deployment Screw with Male Interface.
Figure 13:
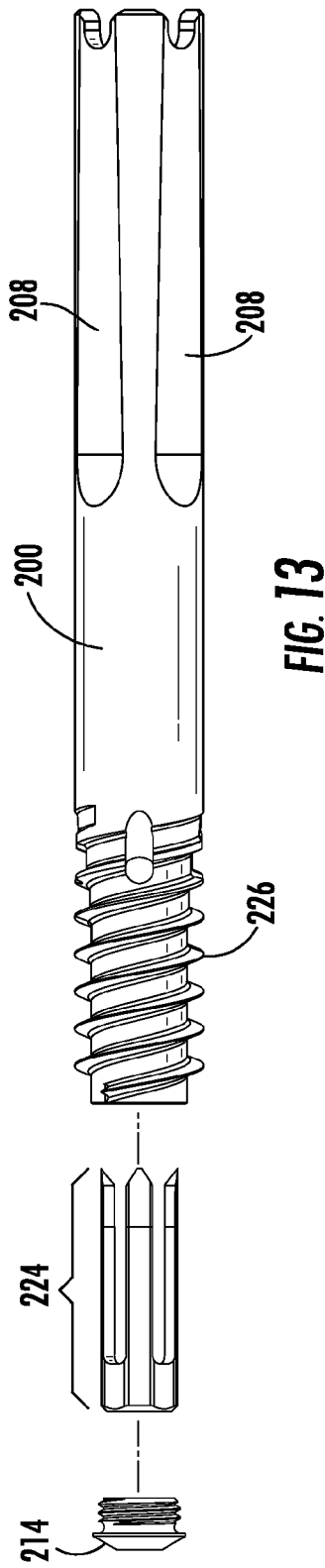
FIG. 13 illustrates an exploded side view of the Intramedullary Nail System including Tang-deployment Screw with Male Interface.
Figure 14:
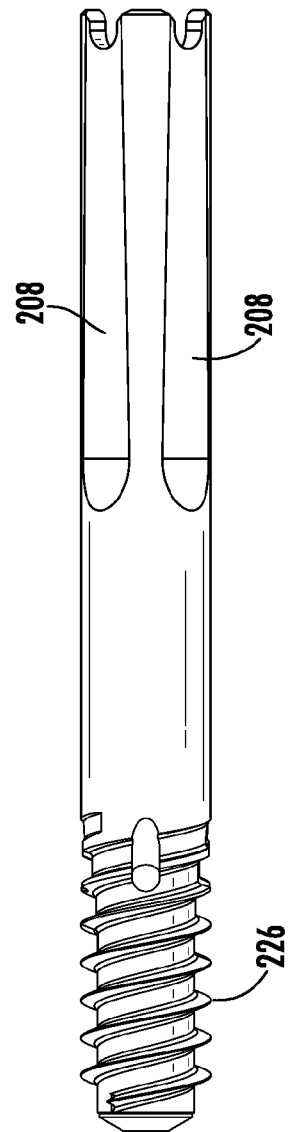
FIG. 14 illustrates an assembled side view of the Intramedullary Nail System including Tang-deployment Screw with Male Interface.

Referring to FIG. 12, the lag screw 200 will be further described. The lag screw 200 includes anti-rotation flats 208. In one embodiment the lag screw 200 includes four anti-rotation flats 208, oriented at 90 degree increments relative to one-another. There is neither a requirement that the number of anti-rotation flats 208 be four, nor that the anti-rotation flats 208 be oriented at 90 degrees from each other. But the orientation of the flats is related to the relative position of the tang portals 222 and thus the tangs 224. Viewing the lag screw 200 from one end, the anti-rotation flats 208 are located at 0, 90, 180, and 270 degrees. The tang portals 222 are located at 45, 135, 225, and 315 degrees. In other embodiments of the lag screw 200, the angular relationship of the anti-rotation flats 208 to the lag screw portals 222 is other than 45 degrees.

Figure 24:
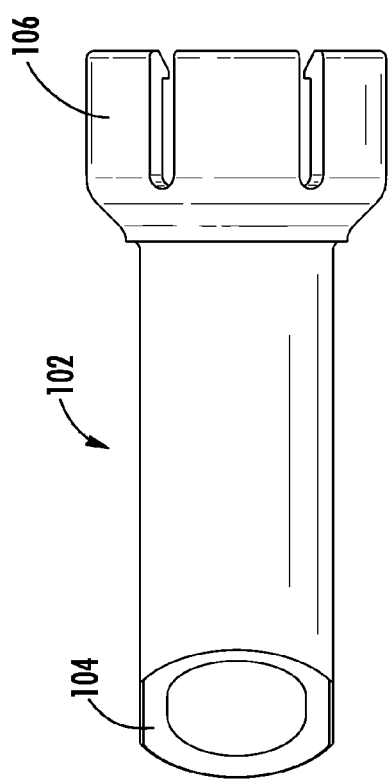
FIG. 24 illustrates a side view of the lock screw button.
Figure 26:
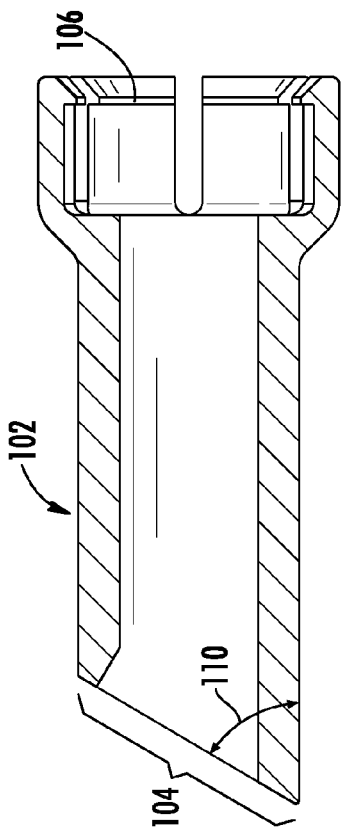
FIG. 26 illustrates a cross-sectional view of the lock screw button.
Figure 23:
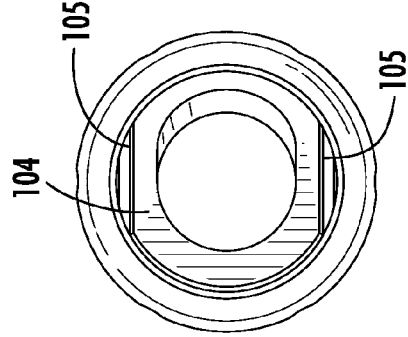
FIG. 23 illustrates an end-on view of the distal end of the lock screw button.
Figure 27:
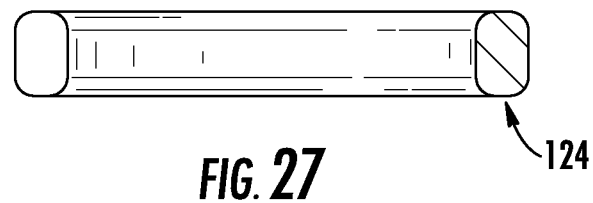
FIG. 27 illustrates a cross-sectional view of the lock screw thread locking element.
Figure 28:
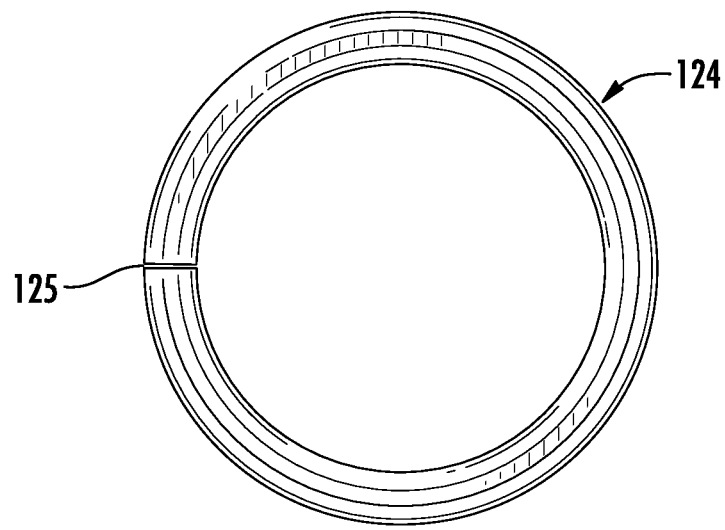
FIG. 28 illustrates a top view of the lock screw thread locking element.

Referring to FIGS. 2, 3, 12, and 19-28, the lock screw assembly will be discussed. The lock screw assembly consists of the lock screw body 100, lock screw button 102, and lock screw thread locking element 124. It is the interaction between these parts that creates a mechanism that is lockable but still easily adjustable. While the lock screw body 100 and lock screw button 102 are two separate parts, during assembly the two parts are affixed to one another using any number of mating provisions. The lock screw button 102 ends in barbs 106 (see FIG. 24) that slide over the lock screw ramp 116. The barbs 106 are separated by gaps to allow for greater flexibility. It is anticipated that as an alternative to barbs 106 with gaps, the lock screw button be made of a soft material that stretches to couple with the lock screw body 100.

Snapping into the lock screw notch 114 creates a connection between the lock screw body 100 and lock screw button 102. After the lock screw button barbs 106 are engaged, the lock screw body 100 and lock screw button 102 do not easily separate. This connection permits rotation, allowing the lock screw body 100 to rotate with respect to the lock screw button 102.

To maintain alignment between the lag screw 200 and the lock screw button face 108, there is a lock screw button flat 105 (see FIG. 23) on two sides of the lock screw button 102. These two flat surfaces correspond to two flat surfaces on the inside of the nail proximal shaped bore 8 (see FIG. 3). In this embodiment, the nail proximal shaped bore 8 has what is known as a "Double-D" shape. Double-D is a description for a shape created by dual flat surfaces that interrupt a round bore. This shape prevents rotation of the lock screw button 102 during adjustment through interaction of the flat surfaces 8/105, while allowing axial travel to engage the flat surfaces 208 of the lock screw 200.

The lock screw button 102 secures the position of the lag screw 200 relative to the nail 40. The anti-rotation flats angle 209 (FIG. 12) interacts with the lock screw button face 104, allowing the distal end of lag screw 200 to slide only toward the nail body 42, preventing rotation but allowing for fracture compression. Thus, longitudinal translation, or sliding, of the lag screw 200 is allowed while preventing rotation of the lag screw 200 relative to the nail 40. This sliding avoids penetration of the femoral head by the proximal end of the lag screw 228 as the fracture compresses from patient load bearing and prevents the lag screw assembly from hindering compression of the fracture-line near the femoral head.

The lock screw button face angle 110 corresponds to the lag screw centerline to nail centerline angle 230, with compensation for the anti-rotation flats angle 209.

During surgery, the surgeon chooses whether or not the use the position of the lag screw 200 to provide fracture compression. Whether or not the surgeon chooses to apply compression, the lag screw 200 must be set in either a fixed or sliding fixation type. A fixed lag screw position prevents both rotation and sliding of the lag screw 200 relative to the nail body 40. A fixed position is achieved by fully tightening the lock screw button 102 against the most proximal anti-rotation flat 208.

Alternatively, the surgeon may use a sliding lag screw position 200 that allows free lateral sliding of the lag screw 200, while still preventing rotation. A sliding lag screw position is made possible by the design of the anti-rotation flats 208. The anti-rotation flats 208 have an angle with respect to the lag screw centerline 32, shown as anti-rotation flats angle 209. In this embodiment, this angle is 0.5 degrees. The result of the anti-rotation flats angle 209 is that the anti-rotation flats distal breadth 202 is greater than the anti-rotation flats proximal breadth 204. It is the interaction of the sloped anti-rotation surfaces 208 with the lock screw button 102 that controls the amount of relative longitudinal motion permitted between the nail assembly and lag screw assembly.

The lock screw thread locking element 124 is made of a material that is softer than the material used in the nail proximal internal threads 84, into which the lock screw thread locking element 124 threads. Such softer materials include certain metals, such as copper, or non-metal materials, such as plastic. The lock screw thread locking element 124 is also sized to be slightly too large for the nail proximal bore 80. This creates an interference fit between the lock screw thread locking element 124 and the nail proximal internal threads 84. The interference fit in turn creates resistance, preventing the lock screw from rotating freely and loosening the connection between lock screw button 102 and the lag screw 200. The lock screw thread locking element 124 includes a gap 125 to aid in assembly. It is anticipated that the lock screw thread locking element be made from two or more separate pieces, or without a gap 125 at all if the lock screw thread locking element 124 is sufficiently flexible to be stretched over the lock screw body 100.

All the internal parts of the nail assembly are optionally cannulated, or with a central bore, allowing the nail to be nearly entirely preassembled but still able to be installed over a guide wire. Cannulated parts may include lock screw body 100, lock screw button 102, lock screw thread locking element 124, thrust washer 126, nail 40, nail distal end cap 62, nail proximal end cap 82, nail actuation shaft 142, nail tang distal threaded hub 152, nail tang proximal threaded hub 153, and nail thrust washer 154. It is not required that the parts be cannulated, but rather is done to ease installation by the surgeon, in turn lowering surgery time.

Similarly, the lag screw body 201, lag screw end cap 214, and the hub of the law screw tangs 224 are optionally cannulated, allowing installation over a guide wire.

Figure 29:
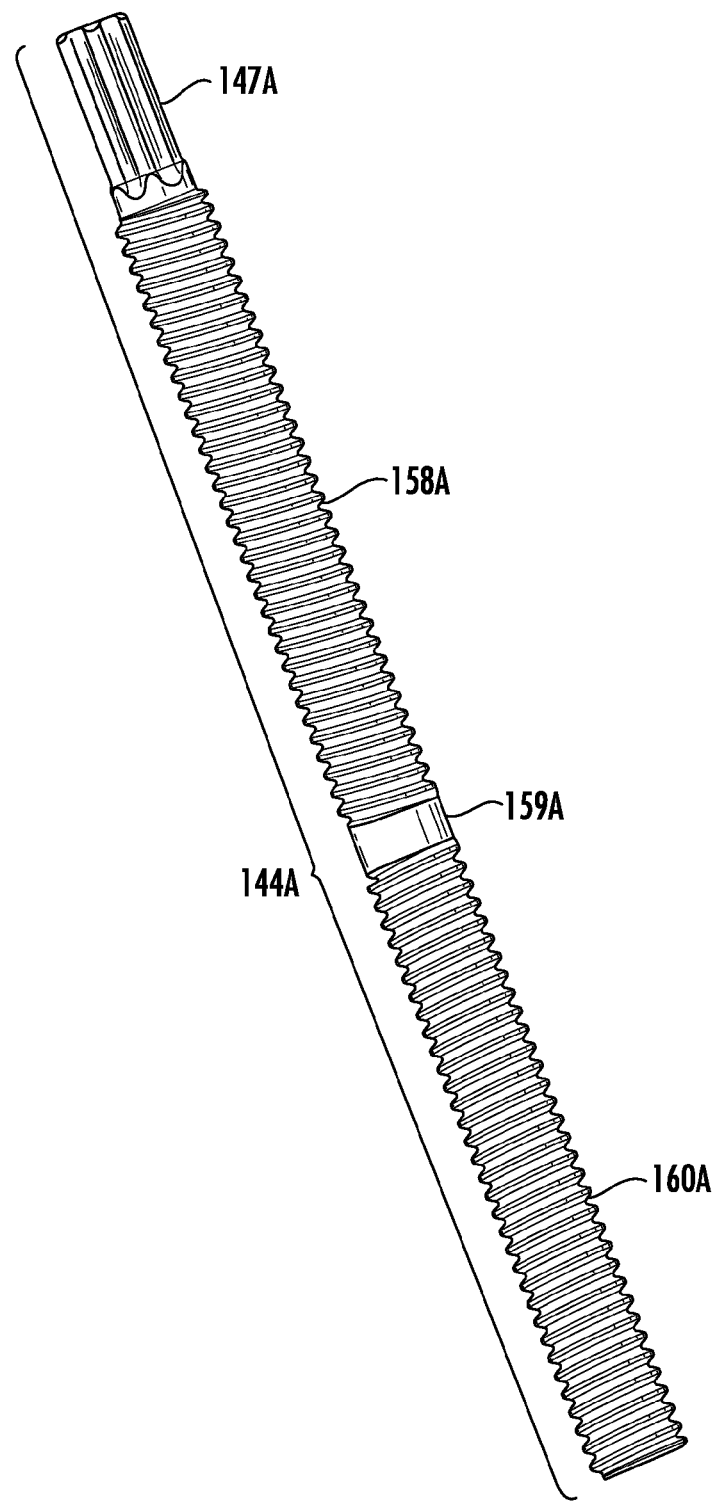
FIG. 29 illustrates a view of the modified nail actuator screw.

FIG. 29 illustrates a view of the modified nail actuator screw 144A. Referencing FIG. 2, the modified nail actuator screw 144A, with the parts described below, replaces distal opposing nail tangs 140, nail actuator screw 144, nail tang distal threaded hub 152, nail tang proximal threaded hub 153, nail thrust washer 154, and proximal opposing nail tangs 156 of the standard nail actuator screw assembly.

The modified nail actuator screw 144A has a nail actuator screw drive head 147A, shown as male Torx type head. As with the standard nail actuator screw, there is a nail actuator screw proximal thread 158A and nail actuator screw distal thread 160A, separated by a nail actuator screw stop 159A.

In the preferred embodiment, the modified nail actuator screw 144A is non-cannulated, or solid. As discussed above for the reasoning behind the use of the coupler 250, any removal of material for such a small-diameter screw results in excessive weakening.

Figure 30:
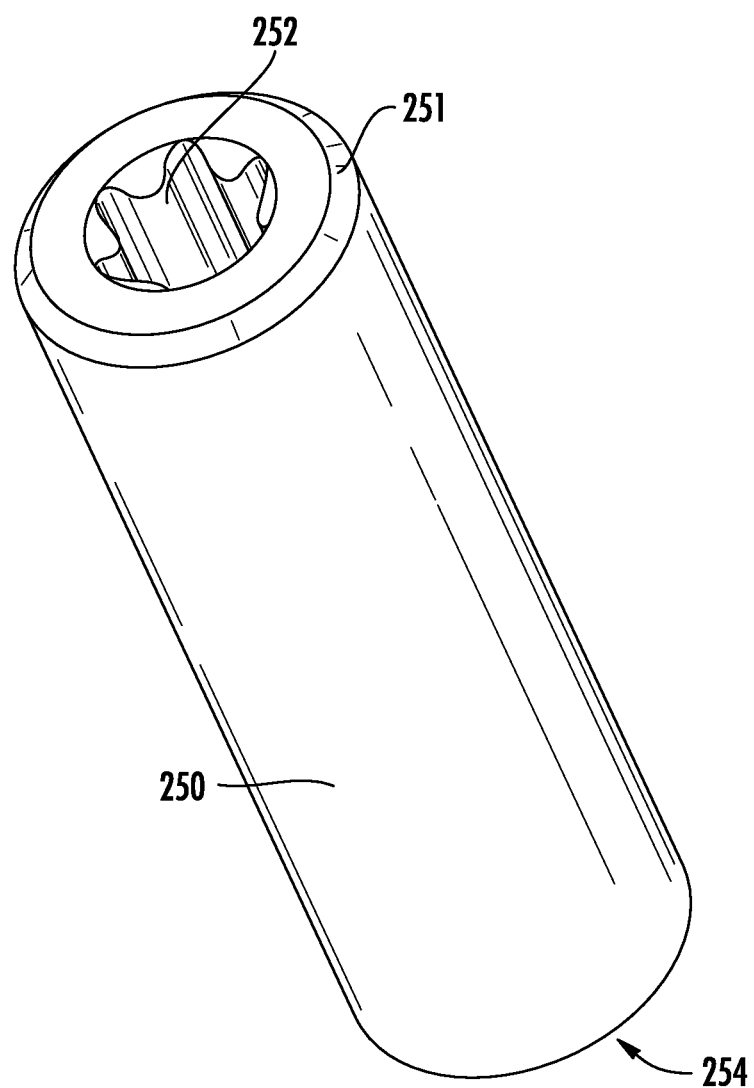
FIG. 30 illustrates a view of the coupler.

FIG. 30 illustrates a view of the coupler 250. The coupler 250 is shown with a coupler first interface 252 and a coupler second interface 254.

The coupler interfaces 252/254 are shown as hexalobular profiles, also known as Torx fitting. The benefits of the shape in this application are numerous.

First, given the hardness of the material used for the coupler 250, the rounded profile of the hexalobular profile allows for machining using spinning tools, rather than the broaching required for flat surfaces such as hex shapes.

Second, a hexalobular shape is resistant to cam out, which is the tendency of a screwdriver or other rotational tool to climb out of the interface during tightening. Phillips screwdriver heads are the typical example of an interface with a tendency to cam out.

Third, this hexalobular shape is not used for the nail deployment driver of the larger nails that do not use coupler. Using different profiles minimizes the chance that the surgeon will select the incorrect drive.

Finally, due to a greater bearing surface, Torx transmits torque more effectively than a hex drive of equivalent size.

Figure 31:
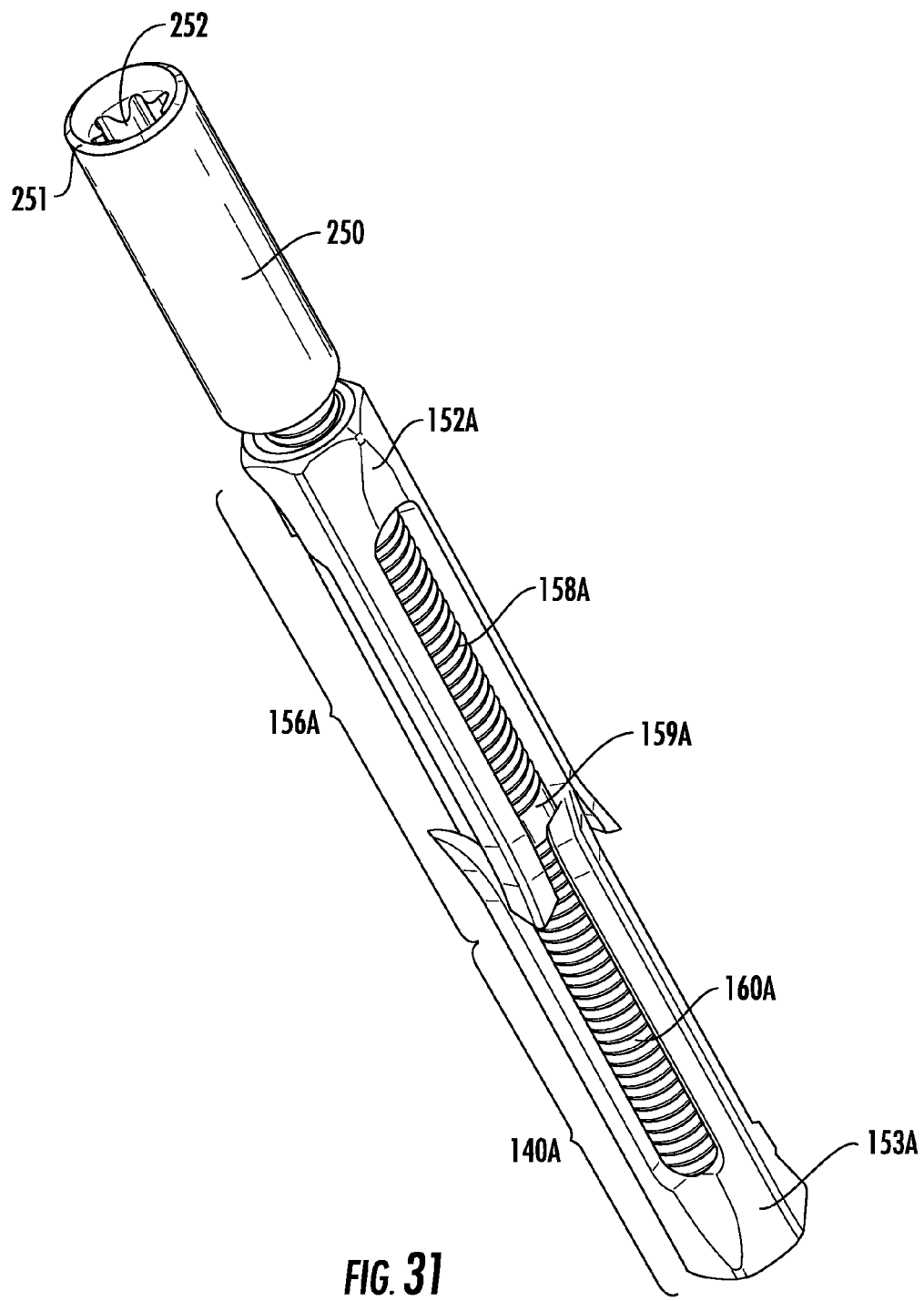
FIG. 31 illustrates a view of the modified nail actuator screw, assembled with the coupler, proximal opposing nail tangs, and distal opposing nail tangs.

FIG. 31 illustrates a view of the modified nail actuator screw, assembled with the coupler, proximal opposing nail tangs, and distal opposing nail tangs.

Shown is coupler 250, with coupler second interface 254 (not shown) mated to nail actuator screw drive head 147A (not shown). Nail tang distal threaded hub 152A interfaces with nail actuator screw proximal thread 158A, nail tang proximal threaded hub 153A interfaces with nail actuator screw distal thread 160A.

Also shown are modified distal opposing nail tangs 140 and modified proximal opposing nail tangs 156.

The modified parts used in the modified nail actuator screw are analogous to the non-modified parts described above, but of smaller size for use in nails of smaller diameter.

Figure 2:
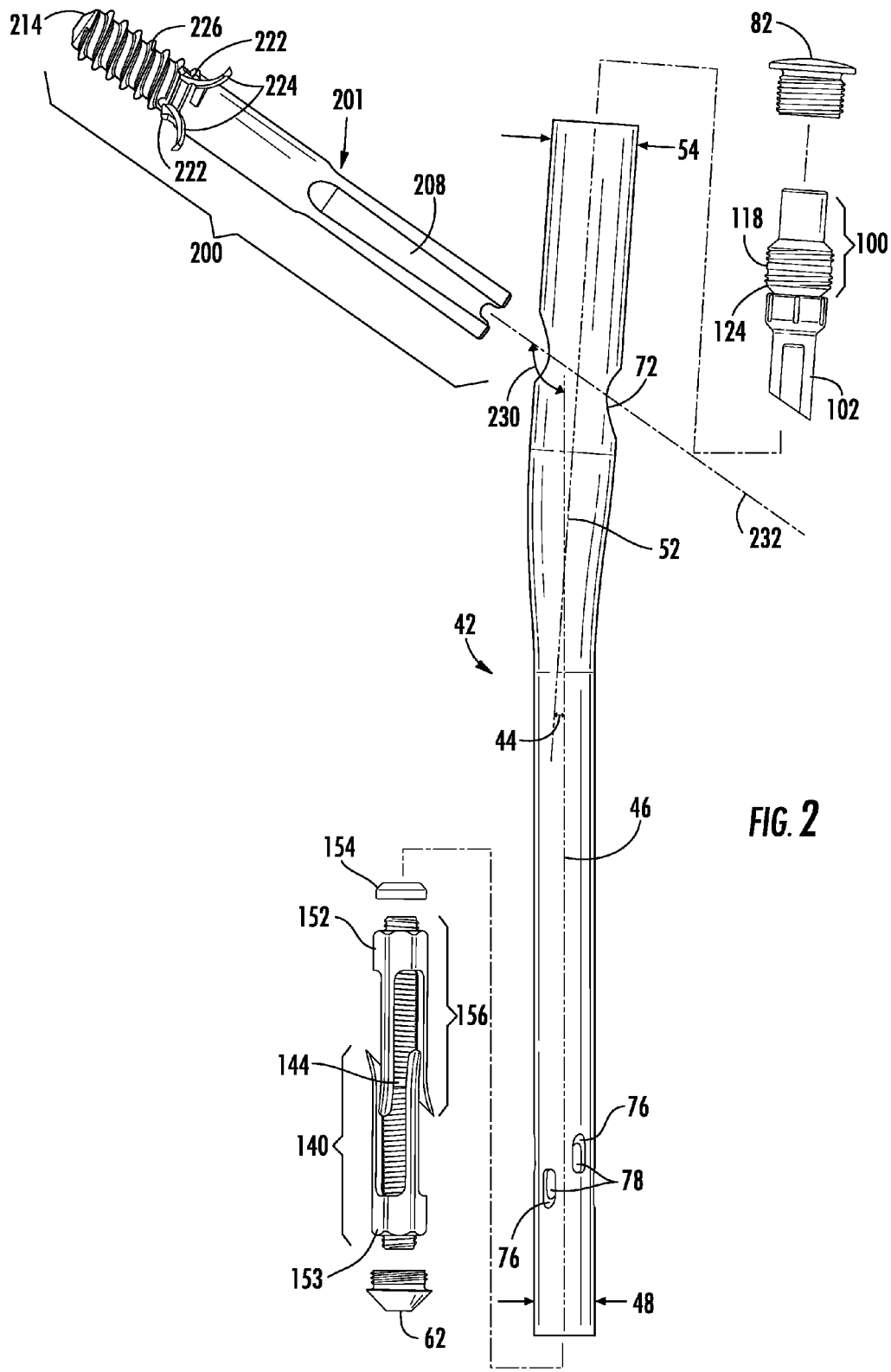
FIG. 2 illustrates an exploded view of the Intramedullary Nail System including Tang-deployment Screw with Male Interface.
Figure 3:
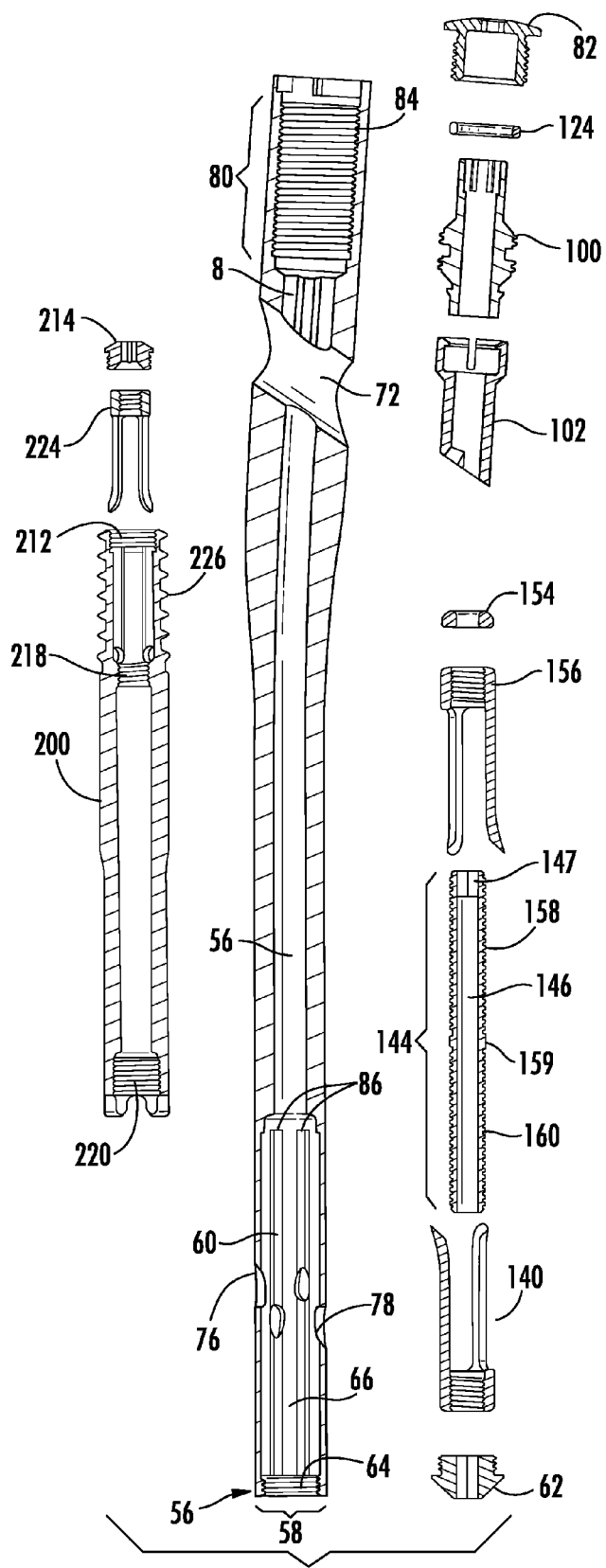
FIG. 3 illustrates an exploded and cross-sectional view of the Intramedullary Nail System including Tang-deployment Screw with Male Interface.
Figure 4:
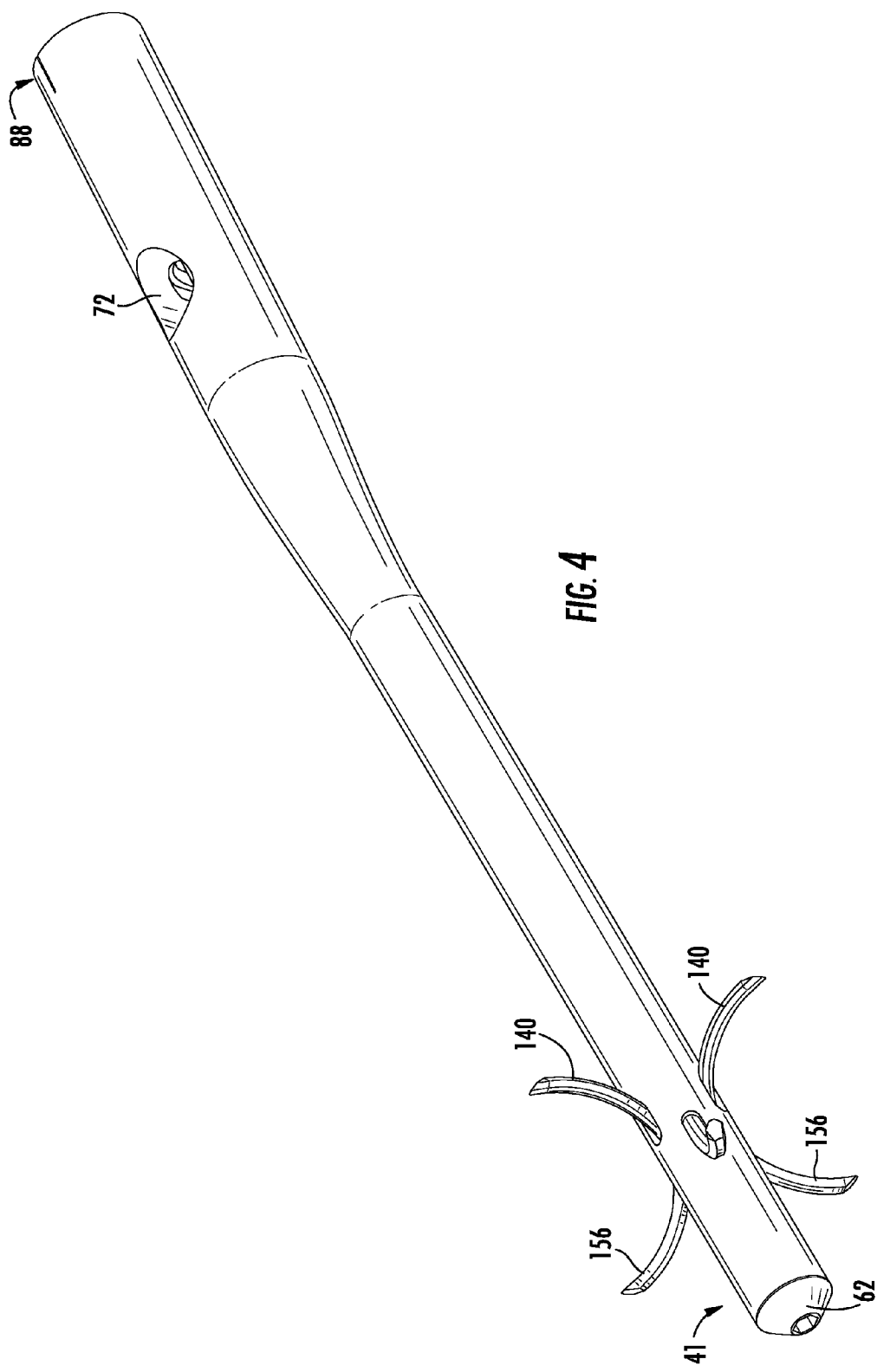
FIG. 4 illustrates an isometric view of the Intramedullary Nail System including Tang-deployment Screw with Male Interface.
Figure 5:
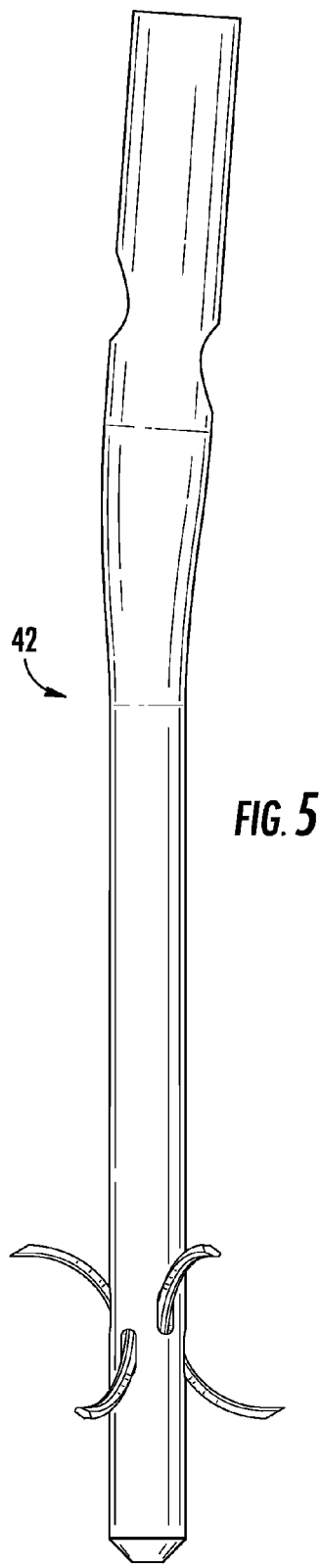
FIG. 5 illustrates a first side view of the Intramedullary Nail System including Tang-deployment Screw with Male Interface.
Figure 6:
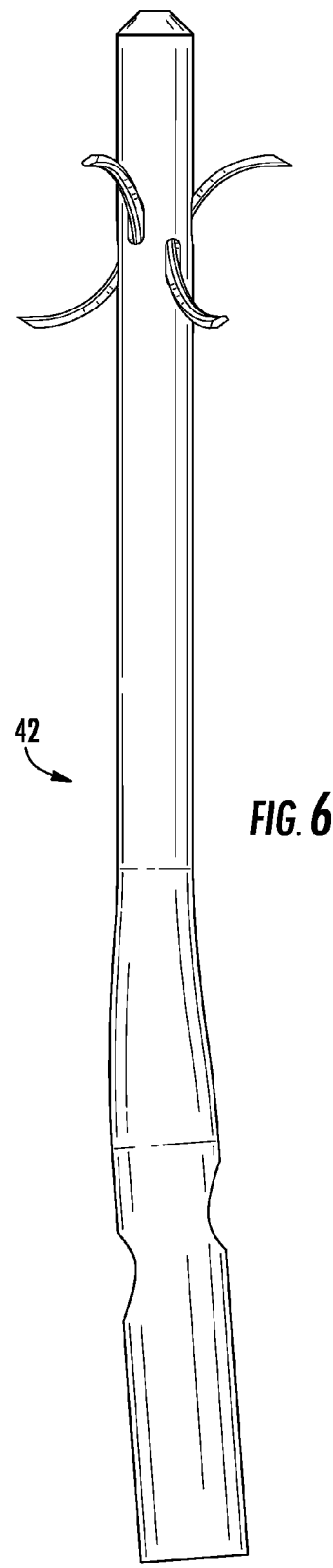
FIG. 6 illustrates a second side view of the Intramedullary Nail System including Tang-deployment Screw with Male Interface.
Figure 7:
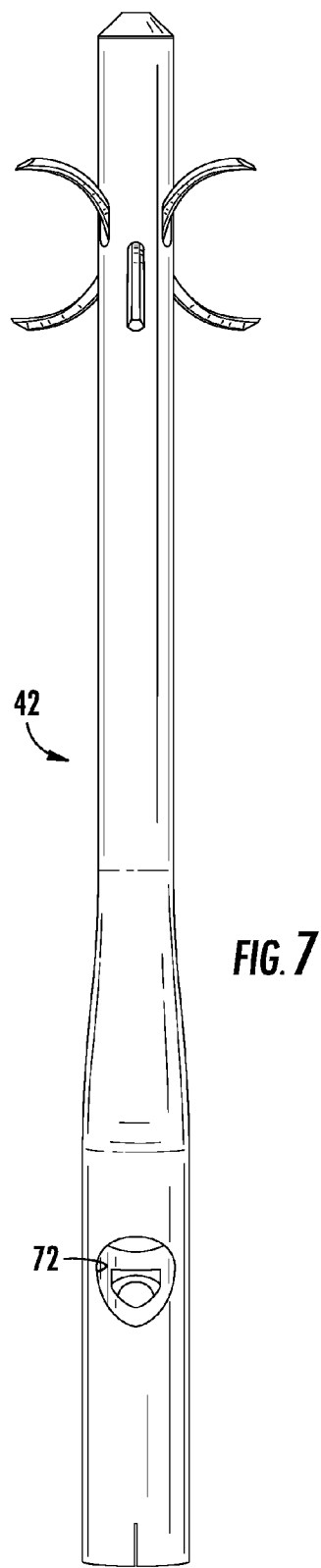
FIG. 7 illustrates a top view of the Intramedullary Nail System including Tang-deployment Screw with Male Interface.
Figure 8:
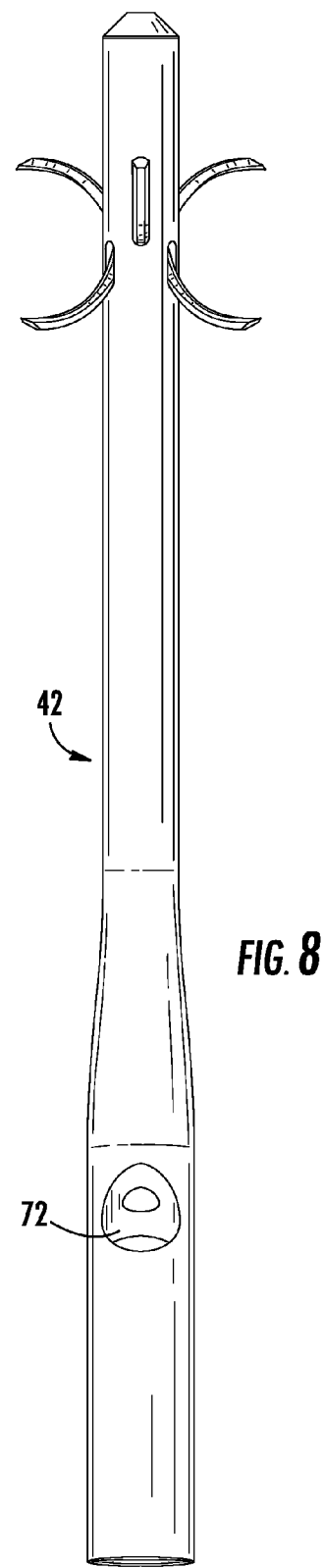
FIG. 8 illustrates a bottom view of the Intramedullary Nail System including Tang-deployment Screw with Male Interface.
Figure 9:
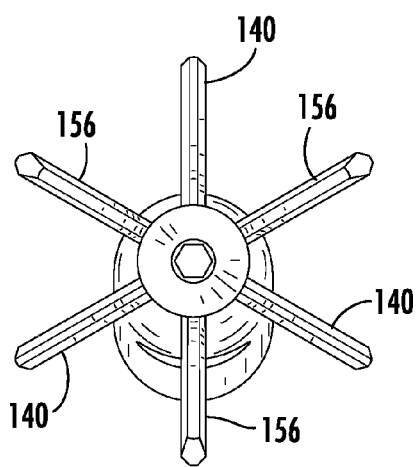
FIG. 9 illustrates an end-on view, distal end, of the Intramedullary Nail System including Tang-deployment Screw with Male Interface.
Figure 10:
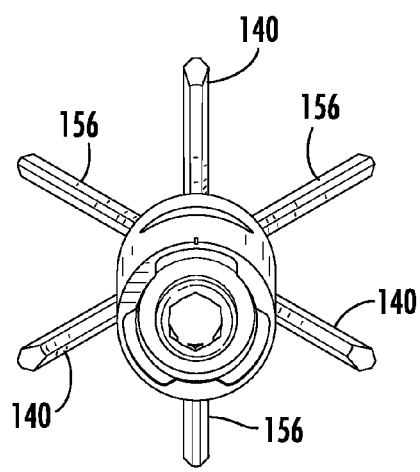
FIG. 10 illustrates an end-on view, proximal end, of the Intramedullary Nail System including Tang-deployment Screw with Male Interface.
Figure 11:
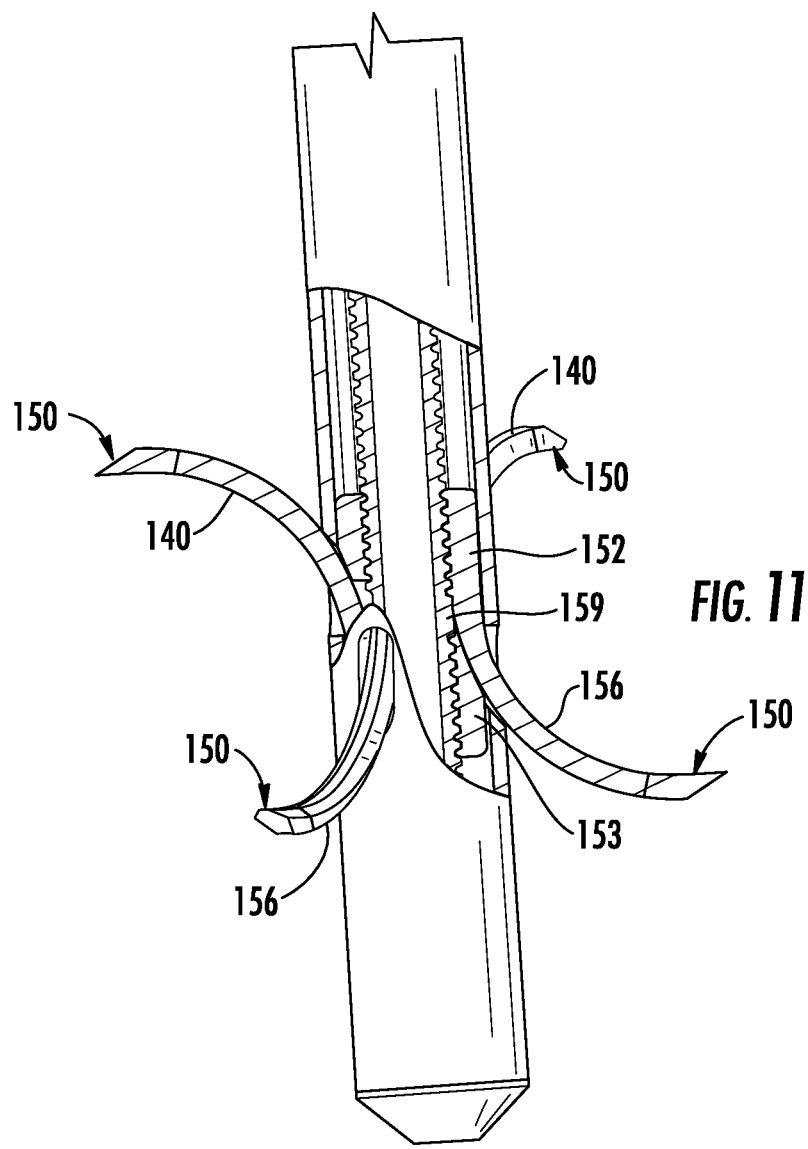
FIG. 11 illustrates a partial cross-section of the nail tang actuation region of the Intramedullary Nail System including Tang-deployment Screw with Male Interface.

The coupler 250 takes the place of the thrust washer 154, shown in FIG. 2. Despite the net forces being nearly zero, there is likely a small axial force by the nail actuation screw 144A against its ends. This force is transmitted to the nail body 40 by, on the proximal end, the coupler 250, and on the distal end, the nail distal end cap 62. The coupler 250 is designed for operation under sliding friction and spreads out the compressive axial load.

The thrust washer taper 251 acts to center the nail actuation screw 144A within the nail body 40 by self-centering. The coupler 250 remains within the nail 40 at all times following initial assembly. Equivalent elements can be substituted for the ones set forth above such that they perform in substantially the same manner in substantially the same way for achieving substantially the same result. It should be noted that this description is directed at only one possible embodiment and that many others are possible. For example, nail tangs and/or lag screw tangs could have any number of legs, and the lag screw can perform well even without tangs.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device for interconnecting first and second fractured bone segments, the device comprising:
    a nail made of a material, having a proximal end, a distal end, an outer surface, a proximal shaped bore, an axial bore, and a transverse bore;
    one or more extendable nail tangs, each extendable nail tang having a first position substantially within the outer surface of the nail, and a second position penetrating the outer surface of the nail;
    a lag screw for insertion through the transverse bore of the nail, the lag screw having a proximal end, a distal end, and a circumferential outer surface; and
    one or more extendable lag screw tangs, each extendable lag screw tang having a first position substantially within the circumferential outer surface of the lag screw, and a second position penetrating the circumferential outer surface of the lag screw;
    a nail actuator screw, the nail actuator screw including: a screw drive head with a male shape, a proximal thread, a distal thread, and a screw stop between the proximal thread and the distal thread;
    a coupler, the coupler having a first interface and a second interface, the second interface mating to the drive head of the nail actuator screw;
    wherein rotation of the coupler rotates the nail actuator screw, which in turn cases the one or more extendable nail tangs to move from their first position to their second position; and
    wherein the circumferential outer surface of the lag screw further comprises anti-rotation flats, where the anti-rotation flats are planar surfaces having an angle with respect to a centerline axis of the lag screw, creating a taper by virtue of the anti-rotation flats near the distal end of the lag screw being a smaller distance apart than the anti-rotation flats near the proximal end of the screw.

2. The device for interconnecting first and second fractured bone segments of claim 1, wherein the angle of the anti-rotation flats with respect to a centerline axis of the lag screw is 0.5 degrees.

3. The device for interconnecting first and second fractured bone segments of claim 1, wherein the anti-rotation flats are located at 0 degrees, 90 degrees, 180 degrees, and 270 degrees as viewed from the proximal end of the lag screw.

4. The device for interconnecting first and second fractured bone segments of claim 3, wherein the extendable nail tangs are offset by 45 degrees from the anti-rotation flats, resulting in positions at 45 degrees, 135 degrees, 225 degrees, and 315 degrees when in the second position and viewed from the proximal end of the lag screw.

5. The device for interconnecting first and second fractured bone segments of claim 1, further comprising:
a lock screw having a distal end, a proximal end, external threads, and a first mating provision;
a lock screw button having a distal end, a proximal end, a face, and a second mating provision;
wherein the first mating provision and the second mating provision interact to rotatably couple the lock screw to the lock screw button, allowing independent rotation of the lock screw and lock screw button.

6. A device for interconnecting first and second fractured bone segments, the device comprising:
a nail made of a material, having a proximal end, a distal end, an outer surface, a proximal shaped bore, an axial bore, and a transverse bore;
one or more extendable nail tangs, each extendable nail tang having a first position substantially within the outer surface of the nail, and a second position penetrating the outer surface of the nail;
a lag screw for insertion through the transverse bore of the nail, the lag screw having a proximal end, a distal end, and a circumferential outer surface; and
one or more extendable lag screw tangs, each extendable lag screw tang having a first position substantially within the circumferential outer surface of the lag screw, and a second position penetrating the circumferential outer surface of the lag screw;
a nail actuator screw, the nail actuator screw including: a screw drive head with a male shape, a proximal thread, a distal thread, and a screw stop between the proximal thread and the distal thread;
a coupler, the coupler having a first interface and a second interface, the second interface mating to the drive head of the nail actuator screw;
wherein rotation of the coupler rotates the nail actuator screw, which in turn cases the one or more extendable nail tangs to move from their first position to their second position; and
wherein the circumferential outer surface of the lag screw further comprises anti-rotation flats, where the anti-rotation flats are planar surfaces having an angle with respect to a centerline axis of the lag screw, creating a taper by virtue of the anti-rotation flats near the distal end of the lag screw being a smaller distance apart than the anti-rotation flats near the proximal end of the screw; and
wherein the angle of the anti-rotation flats with respect to a centerline axis of the lag screw is 0.5 degrees.

7. The device for interconnecting first and second fractured bone segments of claim 6, wherein the anti-rotation flats are located at 0 degrees, 90 degrees, 180 degrees, and 270 degrees as viewed from the proximal end of the lag screw.

8. The device for interconnecting first and second fractured bone segments of claim 7, wherein the extendable nail tangs are offset by 45 degrees from the anti-rotation flats, resulting in positions at 45 degrees, 135 degrees, 225 degrees, and 315degrees when in the second position and viewed from the proximal end of the lag screw.

9. The device for interconnecting first and second fractured bone segments of claim 6, further comprising:
a lock screw having a distal end, a proximal end, external threads, and a first mating provision;
a lock screw button having a distal end, a proximal end, a face, and a second mating provision;
wherein the first mating provision and the second mating provision interact to rotatably couple the lock screw to the lock screw button, allowing independent rotation of the lock screw and lock screw button.

10. A device for interconnecting first and second fractured bone segments, the device comprising:
a nail made of a material, having a proximal end, a distal end, an outer surface, a proximal shaped bore, an axial bore, and a transverse bore;
one or more extendable nail tangs, each extendable nail tang having a first position substantially within the outer surface of the nail, and a second position penetrating the outer surface of the nail;
a lag screw for insertion through the transverse bore of the nail, the lag screw having a proximal end, a distal end, and a circumferential outer surface; and
one or more extendable lag screw tangs, each extendable lag screw tang having a first position substantially within the circumferential outer surface of the lag screw, and a second position penetrating the circumferential outer surface of the lag screw;
a nail actuator screw, the nail actuator screw including: a screw drive head with a male shape, a proximal thread, a distal thread, and a screw stop between the proximal thread and the distal thread;
a coupler, the coupler having a first interface and a second interface, the second interface mating to the drive head of the nail actuator screw;
wherein rotation of the coupler rotates the nail actuator screw, which in turn cases the one or more extendable nail tangs to move from their first position to their second position; and
wherein the circumferential outer surface of the lag screw further comprises anti-rotation flats, where the anti-rotation flats are planar surfaces having an angle with respect to a centerline axis of the lag screw, creating a taper by virtue of the anti-rotation flats near the distal end of the lag screw being a smaller distance apart than the anti-rotation flats near the proximal end of the screw; and
wherein the anti-rotation flats are located at 0 degrees, 90 degrees, 180 degrees, and 270 degrees as viewed from the proximal end of the lag screw.

11. The device for interconnecting first and second fractured bone segments of claim 10, wherein the angle of the anti-rotation flats with respect to a centerline axis of the lag screw is 0.5 degrees.

12. The device for interconnecting first and second fractured bone segments of claim 10, wherein the extendable nail tangs are offset by 45 degrees from the anti-rotation flats, resulting in positions at 45 degrees, 135 degrees, 225 degrees, and 315 degrees when in the second position and viewed from the proximal end of the lag screw.

13. The device for interconnecting first and second fractured bone segments of claim 10, further comprising:
   a lock screw having a distal end, a proximal end, external threads, and a first mating provision;
   a lock screw button having a distal end, a proximal end, a face, and a second mating provision;
   wherein the first mating provision and the second mating provision interact to rotatably couple the lock screw to the lock screw button, allowing independent rotation of the lock screw and lock screw button.

* * * * *